United States Patent [19]

Pollard, Jr.

[11] 4,409,330
[45] Oct. 11, 1983

[54] MATERIAL AND METHOD FOR REMOVING IMMUNOGLOBULINS FROM WHOLE BLOOD

[75] Inventor: John K. Pollard, Jr., Del Mar, Calif.

[73] Assignee: American Hoechst Corporation, Somerville, N.J.

[21] Appl. No.: 209,872

[22] Filed: Nov. 24, 1980

[51] Int. Cl.$^3$ .................. C12N 11/10; C12N 11/04
[52] U.S. Cl. .................. 435/178; 435/177; 435/182
[58] Field of Search ............. 435/182, 178, 177, 883

[56] References Cited

PUBLICATIONS

Mattiasson et al., J. Applied Biochemistry, 2, 321–335, 1980.
Terman et al., J. Immunology, 124, 795–805, 1980.
Jones et al., Cancer, 46, 675–684, 1980.
Bansal et al., Cancer, 42, 1–18, 1978.
Mattiasson, ACS Symposium Series, 106, 203–220, 1979.
Chenais, Protides of the Biological Fluids, pp. 119–122, 1978.
Bansal et al., Int. J. Artificial Organs, vol. 1, No. 2, 1978, pp. 94–103.

Primary Examiner—John C. Bleutge
Assistant Examiner—Patricia Short
Attorney, Agent, or Firm—Natalie Jensen

[57] ABSTRACT

An immunoadsorbent material comprising inactivated, protein-A bearing *Staphlococcus aureus* immobilized in a polymeric matrix is used to remove IgG immunoglobulins and immune complexes from whole blood.

3 Claims, No Drawings

MATERIAL AND METHOD FOR REMOVING IMMUNOGLOBULINS FROM WHOLE BLOOD

BACKGROUND OF THE INVENTION

Protein A-bearing strains of *Staphlococcus aureus* contain a cell wall polypeptide that binds to the Fc region of many mammalian IgG subclasses and has a high affinity for immune complexes. Recently it has been reported that use of such bacteria in an extracorporeal blood processing technique results in tumor regression in canine mammary adenocarcinoma (Terman et al, The Journal of Immunology, 124, 795–805 (1980)) and reversal of feline leukemia when the technique is used in combination with low dose irradiation (Jones et al., Cancer, 46, 675–684 (1980)).

The blood processing technique involves withdrawing a portion of the total blood volume of the tumor bearing host, separating the blood into plasma and formed elements by centrifugation, running the separated plasma through a biological filter containing heat-killed and formalin-fixed protein A-bearing *Staphlococcus aureus*, and thereafter recombining the treated plasma and formed elements into whole blood which is returned to the host subject.

Although the mechanism of the tumor regressions reported remains unclear, it has been established that serum IgG levels in treated subjects decline immediately after perfusion of the plasma over the bacteria and then rebound above preperfusion levels. Regardless of the mechanism(s) involved, the ex vivo removal of serum IgG and immune complexes appears to be a key factor in the observed clinical improvement in the subjects studied.

The disadvantage of the prior art blood processing technique is that it requires separation of plasma from formed elements prior to perfusion of the plasma. Such a separation step is not only time consuming but also increases the possibility of contamination which could be critical to the treated subject.

It has now been discovered that IgG and immune comlexes can be removed from whole blood thereby eliminating the need to separate the blood into formed elements and plasma prior to removal of the substances from the plasma.

SUMMARY OF THE INVENTION

The present invention relates to an immunoadsorbent material and use of same for removing immunoglobulins and immune complexes from whole blood.

Accordingly, a first aspect of the present invention relates to an immunoadsorbent material comprising inactivated, protein A-bearing *Staphlococcus aureus* bacteria immobilized in a polymeric matrix.

A second aspect of invention relates to a method of treating whole blood to remove IgG immunoglobulins and immune complexes which method comprises contacting the blood with the immunoadsorbent material of the present invention.

The removal of IgG immunoglobulins and immune complexes from whole blood has wide ranging use applications. Because the immunoadsorbent binds the immunoglobulins reversibly, the bound material removed from the blood can be subsequently released from the immunoadsorbent and recovered in pure form by a simple change in pH or ion strength. The present invention can also be utilized to separate one or more immunoglobulins of the IgG class from other immunoglobulins present in the blood.

Still another use application of the present invention involves ex vivo removal of IgG and immune complexes from the blood of mammals afflicted with neoplastic tumors. As discussed earlier, such treatment appears to retard the growth of neoplasms in subjects afflicted with same.

Accordingly, a further aspect of the present invention relates to a method of retarding the growth of neoplasms in subject mammals afflicted with same, which method comprises contacting said subject's blood in an extra-corporeal circulating system with an immnoadsorbent material comprising inactivated, protein A-bearing *Staphlococcus aureus* bacteria immobilized in a polymeric matrix and thereafter transfusing said treated blood into the host subject.

The term "immune complex" as used herein refers to an antigen/antibody complex wherein the antibody is an IgG immunoglobulin.

DETAILED DESCRIPTION

The bacterium employed in the preparation of the immunoadsorbent material of the present invention is a protein A-bearing *Staphlococcus aureus*. While most strains of *Staphlococcus aureus* synthesize protein A, there is marked variation in amount in individual strains. One of the best producers is *Staphlococcus aureus* Cowan I (ATCC-12598), which is the preferred strain for use in the present invention.

The *Staphlococcus aureus* organisms, grown in growth-medium at 37° C. are washed with phosphate buffered saline and then formalin-stablized and heat killed. After fixing, the bacterial cells are stored at 4° C. in phosphate buffered saline containing 0.05% azide.

The immunoadsorbent material of the present invention is prepared by adding a 0.1–20% solution of a suitable polymer in aqueous media to an aqueous suspension of formalin-stabilized, heat-killed protein A-bearing *Staphlococcus aureus*. If necessary, the resulting aqueous suspension may be heated to effect complete solution of the polymer. Polymers that may be employed in the present invention include, for example, agarose, chitosan, polyacrylamide, polyacrylamide derivatives and the like.

The above prepared aqueous suspension is then added to a water immiscible solvent with agitation. If the aqueous suspension has been heated to effect solution of the polymer, the solvent should also be heated prior to addition of the suspension to the solvent. Suitable solvents that may be used include, for example, n-hexane, xylene and the like. Agitation of the resulting dispersion results in aqueous droplets of bacteria and polymer dispersed in water immiscible solvent. Dispersion in certain instances may be facilitated by the presence of a detergent.

The aqueous droplets can be hardened with resultant bead formation by cooling the dispersion to room temperature or by the addition of a gelling agent or cross-linking agent. Gelling agents that may be employed include, for example, acetic anhydride, formaldehyde and the like. Cross-linking agents that may be employed include glutaraldehyde, divinyl sulfone, epichlorohydrin and the like.

The immunoadsorbent material of the present invention can be used to remove IgG immunoglobulins and immune complexes from whole blood by simply contacting the blood with the material.

Such contact is effected by passing the blood over a column packed with beads of the immunoadsorbent material or by mixing the blood with an amount of such beads in a suitable container. The duration of the contact is not bound to critical limits although its value should of course be sufficient to allow all IgG and immune complexes to be adsorbed onto the beads; this duration may normally vary between 1 to 10 minutes.

IgG immunoglobulins and immune complexes bound to the immunoadsorbent can be readily released and recovered by eluting a column of the bound material with 1 M acetic acid/PBS buffer, pH 3.; 0.1 M glycine-HCL buffer, pH 3, may also be used for desorption of bound material.

When the immunoadsorbent material of the present invention is used to remove IgG and immune complexes from the blood of a tumor bearing host mammal, removal is effected utilizing an extracorporeal immunoadsorption system. In such a system, a volume of blood from the tumor bearing host is withdrawn, pumped through a column of immunoadsorbent beads and thereafter collected and transfused back into the host subject by intravenous route.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE 1

*Staphlococcus aureus* Cowan I bacteria (ATCC 12598) are grown in Todd-Hewitt broth, pH 7.9 (Scott Laboratories, Fiskeville, R.I.) which has been sterilized at 121° C. for 15 minutes. Two hundred fifty ml Ehrlenmeyer flasks containing 50 ml sterilized broth per flask are innoculated from primary broth cultures grown at 37° C. without agitation (the primary cultures have been innoculated from Todd-Hewitt agar slant cultures). The resultant 50 ml cultures are incubated at 37° C. with agitation (100 rpm) on a shaker having a circular orbit. Bacterial growth is monitored using a Bausch and Lomb Spectronic-20 spectrophotometer, i.e., samples are withdrawn at 15 minute intervals and the optical density (O.D.) determined at a wavelength of 550 nm. Growth is allowed to proceed until no further increase in O.D. is observed in two consecutive samples. Average cell yields are approximately 10 g (wet weight)/liter.

The cells are collected and washed twice by centrifucation at 9000 rpm for 15 minutes in phosphate-buffered saline (PBS, 150 mM NaCl, 40 mM phosphate), pH 7.2, containing 0.05% (w/v) sodium azide. After resuspension to approximately a 10% (w/v) concentration in PBS-azide, the cells are stirred at 23° C. for 1.5 hours in the presence of 1.5% formalin, washed, and again resuspended to the same concentration in buffer without formalin. The cells are then added to a large Ehrlenmeyer flask to a depth of less than 1.5 cm and killed by rapid swirling in an 80° C. water bath for 5 minutes, followed by rapid cooling in an ice-water bath. After 2 more washes in PBS-azide, the cell suspension is adjusted to a 10% (v/v) concentration. If not used immediately, the cell suspension is stored at 4° C.

EXAMPLE II

The cell suspension prepared according to EXAMPLE I is sedimented and resuspended in water several times in order to remove most of the phosphate buffered saline. After the final sedimentation, sufficient water is decanted so that the settled cells occupy approximately 60% of the total volume. Thereafter, 25 ml of the cell suspension is quickly heated to approximately 80° C. and 25 ml of a hot 3% solution of agarose in water is added to the cell suspension with stirring. The resulting aqueous suspension is immediately added to one liter of warm (i.e., 35° C.) n-hexane containing 100 ml of Witcamide 511 (Witco Chemical Corp.). The hexane mixture is shaken vigorously for approximately 5 minutes or until the formed beads adequately harden. The hexane solution is then decanted from the settled beads which are washed twice with hexane and then three times with methanol. The beads are suspended in water and, with the aid of water rinses, passed through sieves of successively decreasing mesh size to afford gel-like beads having the following diameters: 600–800µ (2 ml); 300–600µ (10 ml); 150–300µ (15 ml); and less than 150µ (10 ml).

EXAMPLE III

A sample of heparinized human whole blood assayed for its total content of IgG and IgG complexes is found to contain 10.2 mg per ml of plasma or 5.6 mg per ml of blood. Ten ml of the whole blood sample is passed through a small column holding a 1.0 ml bed volume of immunoadsorbent beads (diameter=150–300µ) resting on a loosely packed plug of glass wool.

Previous testing of a similar column with a sample of standardized human serum established that 2.6 mg of IgG was bound. It was thus estimated that the column treated with the 10 ml human blood sample would bind less than 5% of the total IgG fraction in the blood sample.

After the 10 ml blood sample is passed through the column, the column is washed three times with 2 ml portions of PBS buffer, pH 7.2. The second and third washes are negative for IgG. Thereafter the column is washed with 1 ml of 1 M acetic acid/PBS buffer, pH 3.0, followed by 4 ml of PBS buffer at pH 7.2.

The eluted material is quantitated with commercial immunodiffusion plates (Calbiochem Behring Corp., La Jolla, CA.) after neutralization to pH 7. The eluted material is found to contain 2.2 mg IgG.

In a parallel experiment, an attempt was made to pass a 10 ml sample of the whole blood through a similar sized column holding a 1 ml bed volume of the commercial immuno-adsorbent, Protein, A-Sepharose® CL-4B (Pharmacia Fine Chemicals, Piscataway, N.J.). The initial flow of blood was extremely slow and stopped after approximately 2 ml passed through.

What is claimed is:

1. An immunoadsorbent material for removing IgG immunoglobulins and immune complexes from whole blood comprising inactivated, protein A-bearing Staphlococcus aureus bacteria immobilized in a polymeric matrix, said material being in the form of gel like beads having an average diameter ranging from 100 to 1000 microns.

2. An immunoadsorbent material according to claim 1 wherein said polymeric matrix is selected from the group consisting of agarose, chitosan, polyacrylamide and polyacrylamide derivatives.

3. An immunoadsorbent material according to claim 2 wherein said polymeric matrix is agarose.

* * * * *